United States Patent [19]

Brickner et al.

[11] Patent Number: 5,652,238
[45] Date of Patent: Jul. 29, 1997

[54] ESTERS OF SUBSTITUTED-HYDROXYACETYL PIPERAZINE PHENYL OXAZOLIDINONES

[75] Inventors: Steven J. Brickner, Portage; Michael R. Barbachyn; Douglas K. Hutchinson, both of Kalamazoo, all of Mich.

[73] Assignee: Pharmacia & Upjohn Company, Kalamazoo, Mich.

[21] Appl. No.: 640,899

[22] PCT Filed: Sep. 27, 1994

[86] PCT No.: PCT/US94/10582

§ 371 Date: May 9, 1996

§ 102(e) Date: May 9, 1996

[87] PCT Pub. No.: WO95/14684

PCT Pub. Date: Jun. 1, 1995

Related U.S. Application Data

[63] Continuation-in-part of Ser. No. 155,988, Nov. 22, 1993, abandoned.

[51] Int. Cl.⁶ .................. A61K 31/495; A61K 31/535; C07D 413/10; C07D 413/14
[52] U.S. Cl. .................. 514/235.8; 514/252; 544/121; 544/337; 544/357; 544/364; 544/367
[58] Field of Search .................. 544/121, 364, 544/367; 514/235.8

[56] References Cited

U.S. PATENT DOCUMENTS

| 4,801,600 | 1/1989 | Wang et al. . |
|---|---|---|
| 4,921,869 | 5/1990 | Wang et al. . |
| 5,164,510 | 11/1992 | Brickner . |
| 5,182,403 | 1/1993 | Brickner . |
| 5,225,565 | 7/1993 | Brickner . |
| 5,547,950 | 8/1996 | Hutchinson et al. . |

FOREIGN PATENT DOCUMENTS

| 312000 | 4/1989 | European Pat. Off. ...... C07D 263/20 |
|---|---|---|
| 316594 | 5/1989 | European Pat. Off. . |
| 352781 | 1/1990 | European Pat. Off. . |

OTHER PUBLICATIONS

WO93/09103, (May 1993).
WO93/23384 (Nov. 1993).
Gregory, WA, et al., J. Med. Chem., 32, 1673–81 (1989).
Gregory, WA, et al., J. Med. Chem., 33, 2569–78 (1990).
Wang, C., et al., Tetrahedron, 45, 1323–26 (1989).
D–H Park, Brittelli, DR, et al., J. Med. Chem, 35, 1156–1165 (1992).

*Primary Examiner*—Robert W. Ramsuer
*Attorney, Agent, or Firm*—Donald L. Corneglio; Martha A. Gammill

[57] ABSTRACT

A compound of structural Formula (I) or pharmaceutically acceptable salts thereof wherein: R is $-C(O)-R^1$, $-PO_3=$ or $-P(O)(OH)_2$; $R^1$ is $C_{1-6}$alkyl, $-N(R^4)_2$, $C_{1-6}$alkyl-$N(R^4)_2$, —phenyl—$N(R^4)_2$, —phenyl-NHC(O)$CH_2NH_2$, $-C_2H_4$-morpholinyl, pyridinyl, $C_{1-6}$alkyl-OH, $C_{1-6}$alkyl-$OCH_3$, $C_{1-6}$alkyl $C(O)CH_3$, $-O-C_{1-6}$alkyl-$OCH_3$, $C_{0-3}$alkyl-piperazinyl (optionally substituted with $C_{1-3}$alkyl), imidazolyl, $C_{1-6}$alkyl-COOH, $-C(CH_2OH)_2CH_3$; $R^2$ and $R^3$ are independently selected from hydrogen or F except at least one of $R^2$ or $R^3$ is F; $R^4$ are independently selected from hydrogen or $C_{1-6}$alkyl. The compounds are water soluble and are useful antimicrobial agents, effective against a number of human veterinary pathogens, including multiply-resistant *staphylococci*, *enterococci* and *streptococci*, as well as anaerobic organisms such as *bacteroides* and *clostridia* species, and acid-fast organisms such as *Mycobacterium tuberculosis*.

12 Claims, No Drawings

1

ESTERS OF SUBSTITUTED-HYDROXYACETYL PIPERAZINE PHENYL OXAZOLIDINONES

This application is a 371 of PCT/US94/10582 wich is a continuation-in-part of U.S. Ser. No. 08/155,988 filed 22 Nov. 1993, abandoned.

BACKGROUND OF THE INVENTION

The subject invention discloses carboxylic and phosphate esters of substituted-hydroxyacetyl piperazine phenyl oxazolidinones. The compounds and their salts are water soluble which makes them particularly useful for IV and oral administration for the treatment of microbial infections. The compounds are effective against a number of human and veterinary pathogens, including multiply-resistant *staphylococci, enterococci* and *streptococci*, as well as anerobic organisms such as *bacteroides* and *clostridia* species, and acid-fast organisms such as *Mycobacterium tuberculosis*. The compounds are particularly useful because they are effective against the latter organism wich is known to be responsible for infections in persons with AIDS.

Information Disclosure Statement

U.S. Pat. Nos. 5,164,510 and related 5,225,565 and 5,182,403 discloses 5'indolinyl-5β-amidomethyloxazolidinones, 3-(fused-ring substituted)phenyl-5β-amidomethyloxazolidinones, and 3-(nitrogen substituted) phenyl-5β-amidomethyloxazolidiones wich are useful as antibacterial agents.

PCT/US93/03570 discloses hydroxyacetyl diazene phenyl oxazolidinoes similar to the subject compounds except that the subject compounds are substituted with carboxylic and phosphate esters (i.e., R is —C(O)—R$_1$, —PO$_3^=$ or —P(O)(OH)$_2$) and are water soluble.

Other references disclosing various oxazolidinones include U.S. Pat. Nos. 4,801,600, 4,921,869, Gregory W. A., et al., *J. Med. Chem.*, 32, 1673–81 (1989); Gregory W. A., et al., *J. Med. Chem.*, 33, 2569–78 (1990); Wang C., et al., *Tetrahedron*, 45, 1323–26 (1989); and Brittelli, et al., *J. Med. Chem.*, 35, 1156 (1992).

European Patent Publication 352,781 discloses phenyl and pyridyl substituted phenyl oxozolidiones.

European Patent Publication 316,594 discloses 3-substituted styryl oxozolidiones.

European Patent Publication 312,000 discloses phenylmethyl and pyridinylmethyl substituted phenyl oxazolidinones.

SUMMARY OF THE INVENTION

In one aspect, the subject invention is a compound of structural Formula I:

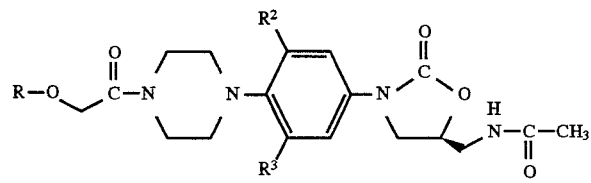

or pharmaceutailly acceptable salts thereof wherein:
R is —C(O)—R$^1$, —PO$_3^=$ or —P(O)(OH)$_2$;
R$^1$ is C$_{1-6}$alkyl, —N(R$^4$)$_2$, C$_{1-6}$alkyl-N(R$^4$)$_2$, -phenyl-N (R$^4$)$_2$, -phenyl-NHC(O)CH$_2$NH$_2$, —C$_2$H$_4$-morpholinyl, pyridinyl, C$_{1-6}$alkyl-OH, C$_{1-6}$alkyl-OCH$_3$, C$_{1-6}$alkyl C(O) CH$_3$, —O—C$_{1-6}$alkyl-OCH$_3$, C$_{0-3}$alkyl-piperazinyl (optionally substituted with C$_{1-3}$alkyl), imidazolyl, C$_{1-6}$alkyl-COOH, —C(CH$_2$OH)$_2$CH$_3$;
R$^2$ and R$^3$ are independently selected from hydrogen or F, except at least one of R$^2$ or R$^3$ is F;
R$^4$ are independently selected from hydrogen or C$_{1-6}$alkyl.

Preferred compounds of the subject invention are where R is —C(O)—R$^1$ and R$^1$ is —CH$_3$, —CH$_2$N(CH$_3$)$_2$, —C$_2$H$_4$-morpholinyl or —CH$_2$OH. Even more preferred is where the compound is an optically pure enantiomer having the S-configuration at C5 of the oxazolidinone ring. More preferable is where one of R$^2$ and R$^3$ is F and the other is hydrogen.

In another aspect, the subject invention is directed toward a method for treating microbial infections in warm blooded animals by administering to a warm blooded animal in need thereof an effective amount of a compound of Formula I as described above. Preferably, the compound is administered in an amount of from about 0.1 to about 100 mg/kg of body weight/day, more preferably, from about 3.0 to about 50 mg/kg of body weight/day.

DETAILED DESCRIPTION OF THE INVENTION

The present invention discloses carboxylic and phosphate esters of substituted-hydroxyacetyl piperazinyl phenyl oxazolidinones of structural Formula I as defined above. The compounds are useful antimicrobial agents, effective against a number of human and veterinary pathogens, including multiply-resistant *staphylococci, enterococci* and *streptococci*, as well as anaerobic organisms such as *bacteroides* and *clostridia* species, and acid-fast bacteria such as *Mycobacterium tuberculosis*. The compounds are designed to be aqueous soluble such that they can be administered by intravenous or oral means.

With respect to the above definition, C$_{1-6}$alkyl is methyl, ethyl, propyl, butyl, pentyl, hexyl and isomeric forms thereof.

Pharmaceutically acceptable salts means salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate, sodium or potassium, ammonioum salt and the like. These salts may be in hydrated form.

The most preferred compounds of the series would be prepared as the optically pure enantiomers having the (S)-configuration at C5 of the oxazolidinone ring. More preferably the compounds have only one of either R$^2$ and R$^3$ as fluorine. The compounds of this invention have an aqueous solubility of greater than 1 mg/ml, more preferably, greater than 4 mg/ml.

Optically pure material could be obtained either by one of a number of asymmetric syntheses or alternatively by reolution from a racemic mixture by selective crystallization of a salt form, for example, intermediate amine 12 (as described in Example 1) with an appropriate optically active acid such as dibenzoyl tartrate or 10-camphorsulfonic acid, followed by treatment with base to afford the optically pure amine.

Commercially available difluoronitrobenzene is treated with excess piperazine to afford a displacement product. Reduction of the nitro group with the ammonium formate-Pd/C regent system or hydrogen-Pd/C affords an aniline derivative. Protection of this aniline derivative affords a bis-(benzyloxy carbonyl) (CBZ) derivative which is treated with nBuLi in THF or ether at −78° to −15° C., then R-glycidyl butyrate is added, and the mixture stirred overnight at 20° C., to give optically active 5-(R)-hydroxy methyl oxazolidinone. Mesylation of 5-(R)-hydroxy methyl oxazolidinone under classical conditions affordes a mesylate which undergoes smooth displacement with sodium azide to form an azide. Reduction of the azide by hydrogenation over Pd/C gives an amine which can be acylated in situ with acetic anhydride and pyridine to afforded a CBZ-protected oxazolidinone intermediate, (S)-N-3-((3-fluoro-4-(4-(carbobenzyloxy)-1-piperazinyl)phenyl)-2-oxo-5-oxazolidinyl)methyl)acetamide. More preferred, the aminomethyloxazolidinone is prepared by displacement of the mesylate with potassium phthalimide to give a phthalimide. Treatment of this phthalimide with aqueous methylamine gives the amine.

Deprotection of the N-carbobenzyloxy with Pd/C and hydrogen afforded the key intermediate for analog preparation, (S)-N-3-((3-fluoro-4-(1-piperazinyl)phenyl)-2-oxo-5-oxazolidinyl)methyl)acetamide (22).

These compounds are useful for treatment of microbial infections in humans and other warm blooded animals, under both parenteral, topical and oral administration.

The pharmaceutical compositions of this invention may be prepared by combining the compounds of Formula I of this invention with a solid or liquid pharmaceutically acceptable carrier and, optionally, with pharmaceutically acceptable adjuvants and excipients employoying standard and conventional techniques. Solid form compositions include powders, tablets, dispersible granules, capsules, cachets and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

Preferably, the pharmaceutical composition is provided employing conventional techniques in unit dosage form containing effective or appropriate amounts of the active component, that is, the compound of Formula I according to this invention.

The quantity of active component, that is the compound of Formula I according to this invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

In therapeutic use for treating, or combatting, bacterial infections in warm-blooded animals, the compounds or pharmaceutical compositions thereof will be administered orally and/or parenterally at a dosage to obtain and maintain a concentration, that is, an amount, or blood-level of active component in the animal undergoing treatment which will be antibacterially effective. Generally, such antibacterially effective amount of dosage of active component will be in the range of about 0.1 to about 100, more preferably about 3.0 to about 50 mg/kg of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two tofour times per day.

The compounds of Formula I according to this invention are administered parenterally, i.e., by injection, for example, by intravenous injection or by other parenteral routes of administration. Pharmaceutical compositions for parenteral administration will generally contain a pharmaceutically acceptable amount of the compound according to Formula I as a soluble salt (acid addition salt or base salt) dissolved in a pharmaceutically acceptable liquid carrier such as, for example, water-for-injection and a buffer to provide a suitably buffered isotonic solution, for example, having a pH of about 3–7. Suitable buffereing agents include, for example, trisodium orthophosphate, sodium bicarbonate, sodium citrate, N-methylglucamine, L(+)-lysine and L(+)-arginine to name but a few representative buffering agents. The compound according to Formula I generally will be dissolved in the carrier in an amount sufficient to provide a pharmaceutically acceptable injectable concentration in the range of about 1 mg/ml to about 400 mg/ml of solution. The resulting liquid pharmaceutical composition will be administered so as to obtain the above-mentioned antibacterially effective amount of dosage. The compounds of Formula I according to this invention, due to their aqueous solubility, are advantageously administered orally in solid and liquid dosage forms.

Antimicrobial activity was tested in vivo using the Murine Assay procedure. Groups of female mice (six mice of 18–20 grams each) were injected intraperitoneally with bacteria which were thawed just prior to use and suspended in brain heart infusion with 4% brewers yeast UC9213 (*Staphylococcus aureus*) or brain heart infusion (Streptococcus species). Antibiotic treatment at six dose levels per drug was administered one hour and five hours after infection by either oral intubation or subcutaneous ("subcut.") routes. Survival was observed daily for six days. $ED_{50}$ values based on mortality ratios were calculated using probit analysis. The subject compounds were compared against a well-known antimicobial (Vancomycin) as a control. The data are shown in Table 1.

TABLE 1

In Vivo Activity of Examples

| Example | $ED_{50}$ mg/kg | VANCOMYCIN $ED_{50}$ mg/kg (subcut.) | ROUTE |
| --- | --- | --- | --- |
| 1 | 5/4 | 2 | oral/subcut. |
| 2 | 9/15 | 5 | oral/subcut. |
| 3 | 16/8 | 8 | oral/subcut. |
| 4 | 2/2 | 2 | oral/subcut. |
| 5 | 7/5 | 5 | oral/subcut. |
| 6 | 2/2 | 2 | oral/subcut. |
| 7 | >20/1 | 6 | oral/subcut. |
| 8 | 10/6 | 5 | oral/subcut. |
| 9 | 2/3 | 1 | oral/subcut. |

TABLE 1-continued

In Vivo Activity of Examples

| Example | ED$_{50}$mg/kg | VANCOMYCIN ED$_{50}$ mg/kg (subcut.) | ROUTE |
| --- | --- | --- | --- |
| 10 | 1/2 | 3 | oral/subcut. |
| 11 | 8/8 | 4 | oral/subcut. |
| 12 | 12/>20 | 5 | oral/subcut. |
| 13 | >20/>20 | 4 | oral/subcut. |
| 14 | 3 | 2 | oral |
| 16 | 4 | 2 | oral |
| 17 | 5/2 | 2/1 | oral/subcut. |
| 18 | 14/>20 | 10 | oral/subcut. |
| 20 | 6/4 | 6 | oral/subcut. |
| 21 | 8/13 | 3 | oral/subcut. |
| 22 | >18/4 | 3 | oral/subcut. |
| 23 | 2/1 | 3 | oral/subcut. |
| 24 | 1 | 2 | oral |
| 25 | 8/15 | 6 | oral/subcut. |
| 26 | 6/3 | 2 | oral/subcut. |
| 27 | 6 | 5 | oral |
| 29 | 9 | 4 | oral |

In Table 1 the compound structures of each of the Examples are shown in Table 2 as follows:

TABLE 2

| Example | R | R$^2$ | R$^3$ |
| --- | --- | --- | --- |
| 1 | C(O)-C$_2$H$_4$-morpholinyl | H | F |
| 2 | C(O)-3-pyridinyl | H | F |
| 3 | C(O)-3-pyridinyl | F | F |
| 4 | C(O)-1-imidazolyl | H | F |
| 5 | C(O)-1-imidazolyl | F | F |
| 6 | C(O)OC$_2$H$_4$OCH$_3$ | H | F |
| 7 | C(O)p-N(CH$_3$)$_2$Ph | H | F |
| 8 | C(O)p-N(CH$_3$)$_2$Ph | F | F |
| 9 | C(O)CH$_2$N(CH$_3$)$_2$ | H | F |
| 10 | C(O)CH$_2$N(CH$_3$)$_2$ | F | F |
| 11 | C(O)(CH$_2$)$_2$N(CH$_3$)$_2$ | H | F |
| 12 | C(O)(CH$_2$)$_3$N(CH$_3$)$_2$ | H | F |
| 13 | C(O)CH$_2$-4-methyl-1-piperazinyl | H | F |
| 14 | C(O)CH$_3$ | F | F |
| 15 | C(O)C$_2$H$_4$C(O)OH | F | F |
| 16 | C(O)C$_2$H$_4$C(O)O$^-$Na$^+$ | F | F |
| 17 | C(O)C$_2$H$_4$C(O)OH | H | F |
| 18 | C(O)C$_2$H$_4$C(O)CH$_3$ | F | F |
| 19 | C(O)C$_2$H$_4$C(O)CH$_3$ | H | F |
| 20 | P(O)(OH)$_2$ | H | F |
| 21 | C(O)p-NH$_2$Ph | H | F |
| 22 | C(O)C(CH$_3$)(CH$_2$OH)$_2$ | H | F |
| 23 | C(O)CH$_2$OH | H | F |
| 24 | C(O)CH$_2$OH | F | F |
| 25 | C(O)CH$_2$OCH$_3$ | H | F |
| 26 | C(O)C$_2$H$_4$-4-morpholinyl | F | F |
| 27 | C(O)CH$_2$-4-morpholinyl | H | F |
| 28 | C(O)p[NHC(O)CH$_2$N(CH$_3$)$_2$]Ph | H | F |
| 29 | C(O)p(-NHC(O)CH$_2$NH$_2$)Ph | H | F |
| 30 | C(O)CH$_3$ | H | F |

EXAMPLE 1

3-(4-Morpholinyl)propionic acid, 2-(4-(4-(5-((acetylamino)methyl)-2-oxo-3-oxazolidinyl)-2-fluorophenyl)-1-piperazinyl)-2-oxoethyl ester, (S)

A 3 liter 3-neck flask fitted with a mechanical stirrer, thermometer and nitrogen inlet was charged with 45.789 g of (S)-N-[[3-fluoro-4-(1-piperazinyl)phenyl]-2-oxo-5-oxazolidinyl]methyl]acetamide and 1.3 liters of CH$_2$Cl. The mixture was cooled in an ice bath and 38 ml of triethylamine was added uner nitrogen, then 28 ml of benzyloxyacetyl chloride was added via an addition funnel over 35 minutes, and the ice bath removed. After 1.5 hours, 500 ml of water was added, the layers were separated, and the organic phase washed with 500 ml of water. The aqueous layers were extracted with methylene chloride and the combined organic layers dried and concentrated which caused the precipitation of product. This was collected, filtered and washed with methylene chloride to yield 57.48 g of pure (S)-N-[[3-fluoro-4-(4-(benzyloxyacetyl)-1-piperazinyl)phenyl]-2-oxo-5-oxazolidinyl]methyl]acetamide.

A 5 L flask was charged with 29.04 g of this product and 2 L of 33% methylene chloride/methanol (v/v) and was evacuated and filled with nitrogen. The 8.1 g of 10% palladium/carbon was added as a slurry in 50 ml of methylene chloride/methanol (1:2, v/v), and the flask evacuated and filled with nitrogen, the evacuated and filled with hydrogen via balloon. The reaction mixture was stirred over night, the flack evacuated and filled with nitrogen, and the mixture filtered over diatomaceous earth, and the filter pad washed with 33% methylene chloride/methanol (v/v) and concentrated to give a white solid. This solid was purified by column chromatography (silica gel packed in chloroform), and gradient eluted with 3–11% methanol/chloroform to give a white foamy solid. This solid was take up in 10% methanol/ethyacetate, and concentrated to dryness several times to give an amorphous white solid, 20.448 g (86.5%) of (S)-N-[[[3-fluoro-4-(4-(hydroxyacetyl)-1-piperazinyl]phenyl]-2-oxo-5-oxazolidinyl]methyl]acetamide, mp 176°–177° C., (hereinafter, referred to as "Intermediate")

The Intermediate, 421 mg (1.07 mmol) was dissolved in 21 mL of pyridine. To this solution was added 13 mg of DMAP, 268 mg (2.14 mmol) of 3-morpholinepropionic acid and 411 mg (2.14 mmol) of 1-ethyl-3-(3-dimethylaminopropyl) carbodiimide hydrochloride. The reaction was allowed to stir at room temperature, under N$_2$ for 15 hours. After this time, the reaction was complete and was concentrated in vacuo. The crude product was purified twice by silica gel chromatography (30 g of silica gel, eluted with 0.5–4% MeOH/CHCl$_3$). After concentration of pure fractions, 372 mg (65%) of the title compound was recovered as a glassy, white solid. mp: 87°–90° C. Auqeous solubility (pH 7, phosphate buffer) was 36 mg/ml.

EXAMPLE 2

Nicotinic acid, 2-[4-[4-[5-[(acetylamino)methyl]-2-oxo-3-oxazolidinyl]-2-fluorophenyl]-1-piperazinyl]-2-oxoethyl ester, (S)-

A mixture of 251 mg (0.637 mmol) of the Intermediate form Ex. 1, 258 mg (1.35 mmol) of 1-ethyl-3-(3-dimethylamino) propylcarbodiimide, 169 mg (1.37 mmol) nicotinic acid and a catalytic amount of 4-dimethylaminopyridine in 5.0 ml of pyridine was stirred for 24 hours at room temperature. After this time, the mixture was concentrated in vacuo and the obtained crude was taken up in methylene chloride and placed upon a 23.5 cm×2.5 cm 40–63 μ silica column. The column was eluted with ethylacetate, 5% methanol/ethylacetate, 10% methanol/ethylacetate, and 20% methanol/ethylacetate (250 ml each). The appropriate fractions were pooled to provide 300 mg (94%) of the title compound as white foamy solid. The solid changed to a glasssy oil at 80°–85° C. then melted at 173°–175° C. Aqueous solubility (pH 7, phosphate buffer) was 0.3 mg/ml but a salt version should have higher solubility.

EXAMPLE 3

Nicotinic acid, 2-[4-[4-[5-[(acetylamino)methyl]-2-oxo-3-oxazolidinyl]-2,6-difluorophenyl]-1-piperazinyl]-2-oxoethyl ester, (S)-6

The subject compound was prepared from (S)-N-[[3-[3,5-difluoro-4-[4-(hydroxyacetyl)-1-piperazinyl]phenyl]-2- oxo-5-oxazolidinyl]methyl]acetamide (preparation described in Ex. 15) in 77% yield (mp=213°–214° C.) following the same procedure as for Example 2. Aqueous solubility (pH 7, phosphate buffer) was 0.05 mg/ml but salt version should have higher solubiltiy.

EXAMPLE 4

1H-imidazole-1-carboxylic acid, 2-[4-[4-[5-[(acetylamino)methyl]-2-oxo-3-oxazolidinyl]-2-fluorophenyl]-1-piperazinyl]-2-oxoethyl ester, (S)-

A mixture of 246 mg (0.624 mmol) of the Intermediate from Ex. 1 and 304 mg (1.875 mmol) of carbonyl diimidazole in 10 ml of tetrahydrofuran was stirred over night. The resulting precipitate was filtered away from the solvent, washed and dried to provide 251 mg (82% yield) of the subject compound; (mp=188°–189° C.) Aqueous solubility (pH 7, phosphate buffer) was 1.4 mg/ml.

EXAMPLE 5

1H-imidazole-1-carboxylic acid, 2-[4-[4-[5-[(acetylamino)methyl]-2-oxo-3-oxazolidinyl]-2,6-difluorophenyl]-1-piperazinyl]-2-oxoethyl ester, (S)-

The subject compound was prepared from (S)-N-[[3-[3,5-difluoro-4-[4-(hydroxyacetyl)-1-piperazinyl]phenyl]-2-oxo-5-oxazolidinyl]methyl]acetamide (preparation described in Ex. 15) in 82% yield (mp=199°–200° C.) following the same procedure as for Example 4.

EXAMPLE 6

Carbonic acid, 2-[4-[4-[5-[(acetylamino)methyl]-2-oxo-3-oxazolidinyl]-2-fluorophenyl]-1-piperazinyl]-2-oxoethyl ester-2-methoxyethyl ester, (S)

To a solution of 175 mg (0.444 mmol) of the Intermediate from Ex. 1 in 5.0 ml methylene chloride at 0° C. under nitrogen was added 0.25 ml (1.79 mmol) triethyamine followed by 129 mg (0.931 mmol) 2-methoxyethyl chloroformate as a solution in 0.5 ml methylene chloride. The mixture was allowed to slowly warm to room temperature over night. After stirring over night, 5 ml of 1N HCl was added and the resulting solvent layers were separted. The aqueous layer was extracted with methylene chloride (2×5 ml). The combined organic layers were washed with brine and dried (MgSO$_4$) then concentrated to an oil. The crude was placed upon a 24 cm×2.5 cm 40–63 µ silica column. The column was eluted with ethylacetate (300 ml), 5% methanol/ethylacetate, 10% methanol/ethylacetate, 15% methanol/ethylacetate, and 20% methanol/ethylacetate (250 ml each). The appropriate fractions were pooled to provide 170 mg (77% yield) of the subject compound as a foamy solid. Part of the solid was crystallized from boiling ethylacetate to provide 65 mg (65% recovery) of the subject compound as a crystalline solid (mp=149°–151° C.). Aqueous solubility (pH 7, phosphate buffer) was 2.9 mg/ml.

EXAMPLE 7

4-dimethylaminobenzoic acid, 2-[4-[4-[5-[(acetylamino)methyl]-2-oxo-3-oxazolidinyl]-2-fluorophenyl]-1-piperazinyl]-2-oxoethyl ester, (S)-

A mixture of 251 mg (0.637 mmol) of the Intermediate from Ex. 1, 181 mg (0.944 mmol) of 1-ethyl-3-(3-dimethylamino) propylcarbodiimide, 181 mg (1.10 mmol) 4-dimethylaminobenzoic acid and a catalytic amount of 4-dimethylamino pyridine in 3.0 ml of pyridine was stirred over night at room temperature. After this time, another 151 mg (0.914 mmol) of 4-dimethylaminobenzoic acid was added and stirring continued over night. After this time another 89 mg (0.464 mmol) of 1-ethyl-3-(3-dimethylamino propylcarbodiimide was added to the mixture. The mixture was stirred for 5 days at room temperature and then warmed in a 50° C. oil bath for one hour. The incomplete reaction mixture was then concentrated in vacuo. The obtained crude was taken up in methylene chloride and placed upon a 24 cm×2.5 cm 40–63 µ silica column. The column was eluted with ethylacetate (250 ml), 10% methanol/ethylacetate (500 ml), 15% methanol/ethylacetate (250 ml), and 20% methanol/ethylacetate (500 ml). The appropriate fractions were pooled to provide 95 mg (41%) of a white solid which was triturated in ethylacetate to provide 75 mg (32%) of the subject compound as a white solid (mp=210°–211° C.). Aqueous solubility (pH 7, phosphate buffer) was 0.01 mg/ml but salt version should have higher solubility.

EXAMPLE 8

4-dimethylaminobenzoic acid, 2-[4-[4-[5-[(acetylamino)methyl]-2-oxo-3-oxazolidinyl]-2,6-difluorophenyl]-1-piperazinyl]-2-oxoethyl ester, (S)-

The subject compound was prepared from (S)-N-[[3-[3,5-difluoro-4-[4-(hydroxyacetyl)-1-piperazinyl]phenyl]-2-oxo-5-oxazolidinyl]methyl]acetamide (preparation described in Ex. 15) in 59% yield (mp=199°–202° C.) following the procedure used for Example 7. Aqueous solubility (pH 7, phosphate buffer) was 0.01 mg/ml but salt version should have higher solubility.

EXAMPLE 9

Glycine, N,N-dimethyl-, 2-[4-[4-[5-[(acetylamino) methyl]-2-oxo-oxazolidinyl]-2-fluorophenyl]-1-piperazinyl]-2-oxoethyl ester, (S)-

The Intermediate from Ex. 1 (250 mg, 0.634 mmol) was dissolved into 8 ml of dry pyridine and ethyl-3-(3-dimethylamino propyl carbodiimide hydrochloride (243 mg, 1.27 mmol), DMAP (16 mg, 0.127 mmol) and N,N-dimethylglycine (131 mg, 1.27 mmol) was added. The mixture was stirred under N$_2$ at ambient temperature for 18 hours. After this time the solvent was removed under reduced pressure to give a gummy residue. The residue was dissolved into CH$_2$Cl$_2$, washed with water and brine. The organic phase was separtated and dried over anhydrous Na$_2$SO$_4$. The solution was filtered and concentrated to give a solid that was purified by recrystallization from CH$_2$Cl$_2$/Et$_2$O. Isolated 220 mg of the subject compound as a white solid. mp=158°–159° C. Aqueous solubility (pH 7, phosphate buffer) was 150 mg/ml.

EXAMPLE 10

Glycine, N,N-dimethyl-, 2-[4-[4-[5-[(acetylamino) methyl]-2-oxo-3-oxazolidinyl]-2,6-difluorophenyl]-1-piperazinyl]-2-oxoethyl ester, (S)-

This material was prepared in the same manner as Example 9, but starting with (S)-N-[[3-[3,5-difluoro-4-[4-(hydroxyacetyl)-1-piperazinyl]phenyl]-2-oxo-5-oxazolidinyl]methyl]acetamide (preparation described in Ex. 15), mp=171°–172° C. Aqueous solubility (pH 7, phosphate buffer) was 4.2 mg/ml.

EXAMPLE 11

3-(Dimethylamino)propanoic acid, 2-[4-[4-[5-[(acetylamino)methyl]-2-oxo-3-oxazolidinyl]-2-fluorophenyl]-1-piperazinyl]-2-oxoethyl ester, (S)-

Methyl 3-(dimethylamino)propionate (2.0 g, 15.2 mmol) was hydrolyzed to the acid by treatment with aqueous NaOH (18.2 mmol, 1.0N solution) at reflux for 2 hours. The solution was cooled to 0° C. via an ice-bath and treated with 1.0N HCl (18.2 mmol). The solution was lyophilized to give a waxy solid that was used without any fruther purification.

The Intermediate from Ex. 1 (400 mg, 1.02 mmol) was dissolved into 10 ml of dry pyridine and the solution was treated with 3-(dimethylamino)propanoic acid (crude material, 239 mg, 2.04 mmol), ethyl-3-(3-dimethylamino) propyl carbodiimide hydrochloride (341 mg, 2.04 mmol) and DMAP (25 mg, 0.204 mmol). The mixture was stirred at ambient temperature under $N_2$ for 2.5 days. After this time the reaction mixture was concentrated under reduced pressure to give a solid residue. The residue was slurried into $CH_2Cl_2$ followed by washing with with water and brine. The clear organic phase was separted and dried over anhydrous $Na_2SO_4$. The dried solution was filtered and concentrated to a gum that was purified by recrystallization from $CH_2Cl_2$/$Et_2O$. Isolated 296 mg of the desired product as a dull white solid. mp=136°–137° C.

EXAMPLE 12

4-(Dimethylamino)butanoic acid, 2-[4-[4-[5-[(acetylamino)methyl]-2-oxo-3-oxazolidinyl]-2-fluorophenyl]-1-piperazinyl]-2-oxoethyl ester, (S)-

The Intermediate from Ex. 1 (400 mg, 1.01 mmol) was dissolved into 10 ml of dry pyridine and the solution was treated with 4-(dimethylamino)butyric acid hydrochloride (341 mg, 2.03 mmol), ethyl-3-(3-dimethylamino)propyl carbodiimide (389 mg, 2.03 mmol) and DMAP (248 mg, 2.03 mmol). The mixture was stirred at ambient temperature under $N_2$ for 40 hours. After this time the reaction mixture was concentrated under reduced pressure to give a gummy residue. The residue was dissolved into $CH_2Cl_2$ followed by washing with water and brine. The organic phase was separted and dried over anhydrous $Na_2SO_4$. Filtered and concentrated to give a glassy residue that was purified by recrystalliztion from $CH_2Cl_2$/$Et_2O$. Isolated 178 mg of the desired product as a white solid. mp=69°–71° C. Aqueous insolubility (pH 7, phosphate buffer) was 34.6 mg/ml.

EXAMPLE 13

(4-Methyl-1-piperazinyl)acetic acid, 2-[4-[4-[5-[(acetylamino)methyl]-2-oxo-3-oxazolidinyl]-2-fluorophenyl]-1-piperazinyl]-2-oxoethyl ester, (S)-

The intermediate from Ex. 1 (400 mg, 1.01 mmol) was dissolved into 12 ml of dry $CH_2Cl_2$ and the solution was cooled to 0° C. via an ice-bath. Next dry pyridine (92 mg, 1.16 mmol) was added followed by chloroacetyl chloride (131 mg, 1.16 mmol) dropwise via syringe. After 30 minutes the mixture was heated to a gentle reflux for 1 hour. The reaction was cooled and poured into a separatory funnel along with additional $CH_2Cl_2$. The solution was washed with 1% aqueous HCl, water and brine. The organic phase was dried over anhydrous $Na_2SO_4$. Filtered and concentrated to a foam that was purified by recrystallization from $CH_2Cl_2$/$Et_2O$. Isolated 407 mg of the intermediate chloroacetyl ester. mp=173°–174° C.

This chloracetyl ester intermediate (303 mg, 0.643 mmol) was dissolved into 7 ml of dry $CH_3CN$ and the solution was cooled to 0° C. via an ice-bath. Next N-methylpiperazine (258 mg, 2.57 mmol) was added and the mixture was stirred at 0° C. for 1 hour followed by warming to room temperature for 3 hours. After this time TLC showed starting material was consumed. The reaction mixture was poured into a separatory funnel along with $CH_2Cl_2$. The solution was washed with water and brine. The organic phase was dried over anhydrous $Na_2SO_4$. Filtered and concentrated to a glassy residue that was purified by recrystallization from $CH_2Cl_2$/$Et_2O$. Isolated 198 mg of the desired product as a white solid. mp=128°–129° C. Aqueous solubility (pH 7, phosphate buffer) was 79.1 mg/ml.

EXAMPLE 14

Acetic acid, 2-(4-(4-(5-((acetylamino)methyl)-2-oxo-3-oxazolidinyl)-2,6-difluorophenyl)-1-piperazinyl)-2-oxoethyl ester, (S)

A solution of the trifluoroacetic acid salt of difluoropiperazine oxazolidinone (preparation in Ex. 15, below) (0.454 g, 0.969 mmol) and potassium carbonate (0.159 g, 2.27 mmol) in 3 ml of methylene chloride was cooled to 0° C. under nitrogen atmosphere. Acetoxyacetyl chloride (0.125 ml, 1.16 mmol) was then added in a dropwise fashion over 3 min via syringe. The solution was allowed to gradually warm to room temperature as it stirred for 48 hours. Residual starting material was present therefore more acetoxyacetyl chloride (0.1 ml, 0.93 mmol) was added and the reaction mixture was stirred for an additional 2.5 hrs. The reaction mixture was then filtered and evaporated to give 0.371 g of crude material which was subsequently purified on a silica column (40–63 μ, 2.5×24 cm, packed and eluted with 5% methanol/ethyl acetate, collected 15 ml fractions) to give 0.107 g (24%) of the desired material as a white solid, mp 193°–195° C., along with 0.096 g (28% recovery) of the difluoropiperazine oxazolidinone free base. Aqueous solubility (pH 7, phosphate buffer) was 1.6 mg/ml.

EXAMPLE 15

Succinic acid, 2-(4-(4-(5-((acetylamino)methyl)-2-oxo-3-oxazolidinyl)-2,6-difluorophenyl)-1-piperazinyl)-2-oxoethyl monoester, (S)

Part 1 demonstrates the preparation steps for difluorointermediates of the invention.

Part 1

(a) 2,6-difluoro-4-nitrobenzene(trifluoromethane)sulfonate 2,6-Difluoro-4-nitrophenol (31.55 g, 180.19 mmol) was combined with $CH_2Cl_2$ (300 mL) and pyridine (29.15 mL, 360.38 mmol). The resultant slurry was cooled to 0° C. in an ice bath and then treated dropwise with triflic anhydride (31.8 mL, 189.2 mmol) over a period of 45 minutes. The reaction was allowed to stir at 0° C. for two hours and then it was stored in the refrigerator (5° C.) overnight. The reaction was determined to be complete by TLC (15% EtOAc/hexane, UV short wave). The reaction mixture was concentrated under reduced pressure, and then treated with both $H_2O$ (50 mL) and EtOAc (50 mL). This mixture was transferred to a separatory funnel with more EtOAc (100 mL) and washed with 1N HCl until the washings were acidic (2×100 mL). The aqueous phases were back-extracted with EtOAc (2×200 mL). The combined EtOAc extracts were combined and then washed again with 1N HCl (400 mL) and once with brine (400 mL). The organic phase was dried of over anhydrous $Na_2SO_4$, filtered and then concentrated to yield 54.092 g of a red-gold oil. Although the oil was prue by NMR, it was combined with crude products from two other runs and chromatographed over silica gel (500 g) packed with 5% EtOAc. Elution with 2 L each of 5% EtOAc and 10% EtOAc afforded a 95% overall yield of the title compound as a pale yellow oil with HRMS (M⁺) calcd for C₇H₂F₅NO₅S 306.9574, found 306.9590.

(b) 1-(tert-butoxycarbonyl)-4-(2,6-difluoro-4-nitrophenyl) piperazine

A solution of 2,6-difluoro-4-nitrobenzene (trifluoromethane)sulfonate (55 g, 179 mmol) in dry DMF (275 mL) was treated with 1-(tert-butoxycarbonyl) piperazine (45.71 g, 250 mmol). The resultant clear yellow solution turned oragne upon the addition of N,N-diisopropylethylamine (47 mL, 269 mmol). The reaction was heated to reflux for 15 hours under N₂. The reaction was determined to be complete by TLC (30% EtOAc/hexane, UV short wave). The reaction mixture was concentrated by dryness and combined with the crude product of another reaction for purification. The crude material was dissolved in hot CH₂Cl₂ (420 mL; some solids unrelated to the product did not dissolve) and then chromatographed on three separate columns (2 columns with 750 g silica gel, packed with CH₂Cl₂, loaded with 180 mL material, and eluted with 1 L each of 1–5% EtOAc/CH₂Cl₂; one column with 250 g silica gel packed with CH₂Cl₂, loaded with 60 mL compound, and eluted with 2.5 and 5% EtOAc/CH₂Cl₂) to give an 87% yield of the title compound as an orange solid with HRMS (M⁺) calcd for C₁₅H₁₉F₂N₃O₄ 343.1343, found 343.1358.

(c) 1-(tert-butoxycarbonyl)-4-[2,6-difluoro-4-(benzyloxycarbonyl)aminophenyl]piperazine The 1-(tert-butoxycarbonyl)-4-(2,6-difluoro-4-nitrophenyl)piperazine (44.7 g, 130 mmol) was dissolved in 20% THF/MeOH (600 mL) in a 2 L flask. Ammonium formate (41 g, 651 mmol) was added portionwise, followed by 10% Pd-C (1.12 g, 2.5 weight %), with cooling in an ice bath. When the addition was completed the ice bath was removed. The flask became slightly warm, and the yellow color disappeared. The reaction mixture was filtered through Celite (washing the filter cake with 500 mL MeOH). The filtrate was concentrated under reduced pressure to give a solid which was then treated with 1 L EtOAc and 500 mL H₂O. The layers were separated and then the organic layer was washed again with H₂O (500 mL) and once with brine (500 mL). The aqueous portions were back-extracted with more EtOAc (2×300 mL). The combined organic extracts were dried over anhydrous Na₂SO₄, filtered and concentrated to yield a yellow solid. The crude material was recrystallized from hot EtOAc/hexane to afford 39.11 g (67%) of the title compound as a pale yellow crystalline solid with mp 171°–172° C.

(d) [3-[3,5-difluoro-4-[4-(tert-butoxycarbonyl)-1-piperazinyl]phenyl]-2-oxo-5-oxazolidinyl]methanol The 1-(tert-butoxycarbonyl)-4-[2,6-difluoro-4-(benzyloxycarbonyl)aminophenyl]piperazine (14.05 g, 31 mmol) was dissolved in dry THF (150 mL) and then cooled to −78° C. (dry ice/acetone). The reaction was next treated with with n-BuLi (21.6 mL, 35 mmol) dropwise over a 25 minute period. The reaction was allowed to stir at −78° C. for 30 minutes and then (R)-(−)-glycidylbutyrate (4.89 mL, 35 mmol) was added dropwise over 7 minutes. The reaction was maintained at −78° C. for an additional 15 minutes and then the bath was removed, allowing the reaction to slowly warm up to room temperature overnight. The reaction was determined to be complete by TLC (5% MeOH/CHCl₃, UV short wave). The reaction mixture was diluted with 500 mL CH₂Cl₂ and then washed with both H₂O (3×300 mL) and brine (300 mL). The aqueous portions were back-extracted with more CH₂Cl₂ (3×400 mL). The combined organic extracts were dried over Na₂SO₄, filtered and concentrated to give a creamy yellow solid. The crude solid was purified by recrystallization from hot EtOAc/hexane to give 11.063 g (85%) of the title compound as a white solid with mp 164°–166° C.

(e) [[3-[3,5-difluoro-4-[4-(tert-butoxycarbonyl)-1-piperazinyl]phenyl]-2-oxo-5-oxazolidinyl]methyl]-p-toluenesulfonate The [3-[3,5-difluoro-4-[4-(tert-butoxycarbonyl)-1-piperazinyl]phenyl]-2-oxo-5-oxazolidinyl]methanol (24.2 g, 59 mmol) was dissolved in pyridine (110 mL) and then cooled to 0° C. (ice bath). Freshly recrystalized p-toluenesulfonyl chloride (13.4 g, 70 mmol) of was added and the reaction was allowed to stir at 0° C. for 2.5 hours under N₂. The flask was then stoppered and stored in the refrigeratior (5° C.) overnight. The reaction mixture became a pale pink slurry. TLC revealed that some alcohol still remained. The reaction mixture was treated with additional p-toluenesulfonyl chloride (1.12 g, 5.85 mmol), catalytic 4-(dimethylamino)pyridine, and 20 mL of dry CH₂Cl₂ to facilitate stirring. After 4 hours at 0° C., the reaction was found to be complete by TLC (5% MeOH/CH₂Cl₃, UV short wave). The mixture was added to 750 mL ice water and the precipitated product isolated via suction filtration, washing it with both water (1 L) and ether (500 mL). After drying in vacuo, 29.921 g (90%) of the title compound was obtained as white solid with mp 150.5°–151.5° C.

(f) [[3-[3,5-difluoro-4-[4-(tert-butoxycarbonyl)-1-piperazinyl]phenyl]-2oxo-5-oxazolidinyl]methyl] methanesulfonate The [3-[3,5-difluoro-4-[4-(tert-butoxycarbonyl)-1-piperazinyl]phenyl]-2-oxo-5-oxazolidinyl]methanol (3.831 g, 9.27 mmol) was dissolved in CH₂Cl₂ (40 mL), cooled to 0° C., and treated with triethylamine (1.74 g, 2.4 mL, 17.22 mmol) under N₂. Methanesulfonyl chloride (1.48 g, 1 mL, 12.92 mmol) was slowly added over 1 min. TLC analysis (20% acetone/CH₂Cl₂) after 0.5 h revealed the reaction to be complete. The reaction mixture was diluted with CH₂Cl₂ (200 mL) and washed with water (3×50 mL) and brine (50 mL), dried over Na₂SO₄, filtered and concentrated in vacuo to furnish the title compound as an off-white solid with HRMS (M⁺) calcd for C₂₀H₂₇F₂N₃O₇S 491.1538, found 491.1543.

(g) [[3-[3,5-difluoro-4-[4-(tert-butoxycarbonyl)-1-piperazinyl]phenyl]-2-oxo-5-oxazolidinyl]methyl]azide The [[3-[3,5-difluoro-4-[4-(tert-butoxycarbonyl)-1-piperazinyl]phenyl]-2-oxo-5-oxazolidinyl]methyl]-p-toluenesulfonate (29.661 g, 52 mmol) was dissolved in dry DMF (125 mL) and then treated with solid NaN₃ (10.19 g, 156 mmol) at room temperature. The reaction was heated to 60° C. for three hours and then allowed to cool to room temperature overnight under N₂. The reaction was found to be complete by TLC (30% EtOAc/hexane, run twice, UV short wave). The reaction mixture was concentrated in vacuo to give a cream colored solid. The crude product was dissolved in 600 mL EtOAc and then washed with both H₂O (2×500 mL) and brine (500 mL). The aqueous portions were back-extracted with more EtOAc (2×400 mL). The combined organic extracts were dried over Na₂SO₄, filtered and concentrated in vacuo to yield 22.41 g (91%) of the title compound as a pale yellow solid with mp 115°–117° C.

Employing essentially identical conditions, the corresponding mesylate was converted to the same azide.

(h) N-[[3-[3,5-difluoro-4-[4-(tert-butoxycarbonyl)-1-piperazinyl]phenyl]-2-oxo-5-oxazolidinyl]methyl] acetamide The [[3-[3,5-difluoro-4-[4-(tert-butoxycarbonyl)-1-piperazinyl]phenyl]-2-oxo-5oxazolidinyl]methyl]azide (22.4 g, 51 mmol) was dissolved in 1 L of EtOAc and then degassed three times with N₂. Next, 10% Pd-C (4.48 g, 20% by weight) was added and the solution was degassed again threee times (with N₂) before replacing the atmosphere with H₂ (balloon). After 3 hours, the reaction was determined to be complete by TLC (20% MeOH/CHCl₃, UV short wave). At this point, pyridine (8.26 mL, 102 mmol) was added, followed by treatment with acetic anhydride (9.64 mL, 102 mmol). The reaction mixture was allowed to stir overnight at room temperature. The reaction was found to be complete by TLC (20% MeOH/CHCl₃, UV short wave). The reaction mixture was filtered through celite (the filter cake was washed with 500 mL EtOAc), the filtrate concentrated down to approximately 600 mL, and washed with H₂O (2×500 mL) and brine (500 mL). The aqueous portions were back-extracted with more EtOAc (2×500 mL). The combined organic extracts were dried over anhydrous Na₂SO₄, filtered and concentrated to give a yellow solid. Recrystallization of the crude product from hot CHCl₃ and hexane afforded 19.167 g (83%) of the difluoro title compound as a white solid with mp 177°–179° C.

Part 2

(S)-N-[[3,[3,5-difluoro-4-[4-(tert-butoxycarbonyl)-1piperazinyl]phenyl]-2-oxo-5-oxazolidinyl]methyl] acetamide (7.1 g, 15.6 mmol) was dissolved in CH₂Cl₂ (20 mL) and then added to a cold solution of trifluroracetic acid (24 mL). The reaction was allowed to stir at 0° C. under N₂ for 15 minutes, and then the ice bath was removed. After stirring at room temperature for 2 hours, the reaction was complete by TLC (10% MeOH/CHCl₃, UV short wave). The solvent was evaporated off in vacuo to give a gummy brown solid. This solid was dissolved in 30% H₂O/acetone, and then treated with the portion wise addition of NaHCO₃ (7.87 g, 93.7 mmol). The reaction was stirred at room temperature for 20 minutes and then the trifluoroacetate salt was treated with benzyloxyacetyl chloride (3.70 mL, 23.4 mmol) added drop wise over 4 minutes. The reaction mixture was allowed to stir overnight under N₂ at room temperature. The reaction mixture was transferred to a separatory funnel with EtOAc (400 mL) and then washed with water (3×250 mL), saturated NaHCO₃ (250 mL), and brine (250 mL). The aqueous portions were back-extracted with both EtOAc and CH₂Cl₂. The organic layers were dried over anhydrous NaSO₄, filtered and concentrated to yield a yellow solid. The solid was adsorbed on silica gel (25 g) and then chromatographed (200 g SG), eluting with a gradient of 1–4% MeOH in 10% CH₃CN/CHCl₃ to give 5.85 g (75%) of (S)-N-[[3-[3,5-difluoro-4-[4-(benzyloxyacetyl)-1-piperazinyl]phenyl]-2-oxo-5-oxazolidinyl]methyl]acetamide as a white solid with a melting point of 172°–173° C.

Next, (S)-N-[[3-[3,5-difluoro-4-[4-(benzyloxyacetyl)-1-piperazinyl]phenyl]-2-oxo-5-oxazolidinyl]methyl] acetamide (3.84 g, 7.6 mmol) was dissolved in hot 10% EtOac/MeOH (150 mL). After degassing the solution three times with N₂, the Pearlman's catalyst (384 mg, 10% by weight) was added. The solution was degassed again and then the atmosphere was replaced with H₂. The reaction was stirred at room temperature for 4.5 hours. At this point, the reaction was found to be complete by TLC (10% MeOH/CHCl₃, UV short wave). The solution was filtered through celite, washing the cake with EtOAc (250 mL). The filtrate was concentrated under reduced pressure to give a white solid. The material was chromatographed on silica gel (150 g), eluting with a gradient of 1–6, 10% MeOH in 10% CH₃CN/CHCl₃ to yield 3.078 g (98%) of (S)-N-[[3-[3,5-difluoro-4-[4-(hydroxyacetyl)-1-piperazinyl]phenyl]-2-oxo-5-oxazolidinyl]methyl]acetamide as a white solid with a melting point of 160.5°–162.5° C.

The prepared product (0.247 g, 0.599 mmol), succinic anhydride (0.092 g, 0.919 mmol) and 4-dimethylaminopyridine (0.024 g, 0.196 mmol) were weighted into a flame dried flask. Pyridine (10 ml) was added and the solution was placed under nitrogen atmosphere. After stirring 24 hrs the reaction was not complete, therefore more succinic anhydride (0.096 g, 0.959 mmol) was added. The reaction mixture was stirred an additional 2 hours at room temperature then was heated at reflux for 35 min. The solvent was then removed via bulb to bulb distillation to give the crude product as a gummy oil. Water (35 ml) and methylene chloride (65 ml) were then added to the crude product, the phases were separted and the organic portion was extracted with sat. sodium bicarbonate (35 ml). This aqueous portion was then acidified with 3M hydrochloric acid and was extracted with ethyl acetate 3×35 ml. These organic portions were combined, dried with MgSO₄, and evaporated to give the desired product which was still slightly contaminated with succinic acid as a white solid (0.169 g). Because of the low recovery the aqueous portion was basified with sat. sodium bicarbonate and extracted with methylene chloride (30 ml). The aqueous poriotn was again acidified with 3M hydrochloric acid and was extracted with ethyl acetate (3×35 ml). The organics were then evaporated to give 0.161 g of white solid which contained the desired product and acetic and succinic acids. The first batch of product was purified by recrystallization from methanol to give 0.120 g (39%) of white solid mp 143°–144° C. The second batch was purified first by column chromatography (silica, 40×63 μ, 2 ml pipette, packed with 5% methanol/ethyl acetate, eluted with ethyl acetate, 5% and 20% methanol/ethyl acetate, collected 2 ml fractions) then by recrystallization from methanol and chloroform to give an additional 0.078 g (25%) of the desired material as a white solid. Aqueous solubility (pH 7, phosphate buffer) was 12.3 mg/ml.

EXAMPLE 6

Succinic acid, 2-(4-(4-(5-((acetylamino)methyl)-2-oxo-3-oxazolidinyl)-2,6-difluorophenyl)-1-piperazinyl)-2-oxoethyl monoester, sodium salt, (S)

The product from Ex. 15 was dissolved in 1 ml of 0.14M sodium bicarbonate and 5 ml of water. This solution was then frozen and lyophilized to give 0.032 g (41%) of the desired material as a white gum.

EXAMPLE 17

Succinic acid, 2-(4-(4-(5-((acetylamino)methyl)-2-oxo-3-oxazolidinyl)-2,6-difluorophenyl)-1-piperazinyl)-2-oxoethyl monoester, (S)

A pyridine solution (5 ml) of the Intermediate from Ex. 1 (0.267 g, 0.677 mmol), succinic anhydride (0.075 g, 0.749 mmol), and 4-dimethylaminopyridine was stirred for 6 days under nitrogen atmosphere. The reaction was then worked up even though there was still starting oxazolidinone present as indicated by tlc. The pyridine was evaporated on the high vacuum, and the residue was taken up in ethyl acetate (15 ml) and sat. sodium bicarbonate (35 ml). The phases were separted, the aqueous portion was acidified to pH 1 with 3M hydrochloric acid and was extracted with ethyl acetate (5×15 ml). These extractions were combined, dried with MgSO₄ and evaporated to give 0.135 g of light pink solid. Because of the low recovery, the aqueous portion was extracted with more ethyl acetate (5×15 ml). These extracts were dried with MgSO₄ and evaporated to give 0.177 g of white solid. The solids were combined and subjected to another aqueous workup in order to upgrade the material. Thus, the solids were dissolved in 10 ml of sat. sodium bicarbonate and 15 ml of ethyl acetate. The phases were separated and the aqueous portion was acidified with 3M hydrochloric acid, which was then extracted with ethyl acetate (5×10 ml). The organic portion was dried with $MgSO_4$, and evaporated to give the desired product (0.130 g, 39%) as a white solid, mp 67°–70° C. Aqueous solubility (pH 7, phosphate buffer) was 28 mg/ml.

EXAMPLE 18

4-Oxo-valeric acid, 2-(4-(4-(5-((acetylamino) methyl)-2-oxo-3-oxazolidinyl)-2,6-difluorophenyl)-1-piperazinyl)-2-oxoethyl ester, (S)

(S)-N-[[3-[3,5-difluoro-4-[4-(hydroxyacetyl)-1-piperzinyl]phenyl]-2-oxo-5-oxazolidinyl]methyl]acetamide (preparation described in Ex. 15) 0.178 g, 0.432 mmol), ethyl-3-(3-dimethylamino)propyl carbodiimide hydrochloride (0.161 g, 0.839 mmol), and 4-dimethylaminopyridine (0.007 g, 0.057 mmol) were weighed into a flame dried flask. Pyridine (3 ml) was added and the system was placed under nitrogen atmosphere, the levulinic acid (0.07 ml, 0.683 mmol) was added. After stirring for 5 days the pyridine was evaporated on the high vacuum to give the crude material as a yellow oil. The quality of the crude material was upgraded on a samll column, (silica, 40×63 µ, 2 ml pipette, packed with ethyl acetate, eluted with methylene chloride, ethyl acetate, and 5% methanol/ethyl acetate, collected 1 ml fractions). The quality was further improved on a second column (mp, silica, 40×63 µ, 1.5×27 cm, packed with ethyl acetate, eluted with ethyl acetate and 5% methanol/ethyl acetate, collected 20 ml fractions) to give white solid which was still slightly contaminated. This solid was recrystallized from ethyl acetate to give 0.152 g (69%) of the desired material as a white solid, mp 130°–133° C. Aqueous solubility (pH 7, phosphate buffer) was 1.2 mg/ml.

EXAMPLE 19

4-Oxo-valeric acid, 2-(4-(4-(5-((acetylamino) methyl)-2-oxo-3-oxazolidinyl)-2-fluorophenyl)-1-piperazinyl)-2-oxoethyl monoester, (S)

The intermediate from Ex. 1 (0.100 g, 0.253 mmol), ethyl-3-(3-dimethylamino)propyl carbodiimide hydrochloride (0.091 g, 0.475 mmol), and 4-dimethylaminopyridine (0.005 g, 0.041 mmol) were weighed into a flame dried flask. Pyridine (3 ml) and levulinic acid (0.04 ml, 0.391 mmol) were added and the system was placed under nitrogen atmosphere. After stirring for 2 days the pyridine was evaporated under high vacuum and the resulting residue was purified on a silica column (40×63 µ1.5×25 cm, packed with ethyl acetate, loaded with methylene chloride and methanol, eluted with ethyl acetate and 5% methanol/ethyl acetate, collected 15 ml fractions) to give 0.136 g of desired product which was then recrystallized from ethyl acetate to give 0.074 g (59%) of the desired material as a white solid, mp 135.5°–138° c. Aqueous solubility (pH 7, phosphate buffer) was 2.29 mg/ml.

EXAMPLE 20

Phosphoric acid, 2-(4-(4-(5-((acetylamino)methyl)-2-oxo-3-oxazolidinyl)-2-fluorophenyl)-1-piperazinyl)-2-oxoethyl ester, (S)

A solution of the Intermediate from Ex. 1 (200 mg, 0.51 mmol) in dry acetonitrile (20 mL) was cooled under nitrogen and treated with 1H-tetrazole (Aldrich) with stirring. In a separte flask, dibenzyl N,N-diethylphosphoramidite (483 mg, 1.52 mmol) was dissolved in 7 mL of dry acetonitrile and was transferred via cannula to the reaction mixture with stirring for 20 hours. The flask was cooled in an ice bath for 30 minutes, and the mixture treated with m-chloroperoxybenzoic acid. After 5 minutes, the ice bath was removed and the mixture stirred for 1.5 hours after which the mixture was cooled to 0° C. and treated with a solution of 15 mg of sodium sulfite in 10 mL of pH 7 buffer. The mixture was diluted with methylene chloride and extracted with water and saturated sodium sulfite solution. The organic layer was dried ($Na_2SO_4$) and concentrated in vacuo to afford a colorless oil. This material was subjected to radial chromatograhy eluting with a methylene chloride-methanol system to afford 250 mg (75%) of the intermediate, phosphoric acid, 2-(4-(4-(5-((acetylamino) methyl)-2-oxo-3-oxazolidinyl)-2-fluorophenyl)-1piperazinyl)-2-oxoethyl ester, dibenylester, (S), as a white rigid foam. TLC: RF=0.51 (20:1 Methylene chloride-methanol). Exact Mass: calc'd for $C_{32}H_{36}FN_4O_8P$: 655.2333. Found 655.2347.

Next, a solution of the prepred intermediate, above, (350 mg, 0.54 mmol) was dissolved in 5 mL of methanol resulting in a clear, colorless solution with a small amount of undissolved amorphous solid material. The solution was treated with 100 mg of 10% palladium on carbon and hydrogen gas at atmosphere pressure for 16 hours. The mixture was filtered through celite washing the filter pad with methanol and concentrated in vacuo to afford a rigid foam. This material was dissolved in water, filtered and lyophilized to afford a white solid, mp 119°–122° C. Aqueous solubility (pH 7, phosphate buffer) was 25.7 mg/ml.

EXAMPLE 21

4-aminobenzoic acid, 2-[4-[4-[5-[(acetylamino) methyl]-2-oxo-3-oxazolidinyl]-2-fluorophenyl]-1-piperazinyl]-2-oxoethyl ester, (S)-

To a mixture of 956 mg (2.426 mmol) the Intermediate from Ex. 1 and 0.7 ml (5.03 mmol) triethylamine in 20 ml of methylene chloride was added 553 mg (2.980 mmol) of 4-nitrobenzoyl chloride as a solid all at once. The mixture was stirred for 21.5 hours at room temperataure. After this time, 10 ml of 1N HCl was added to the mixture and the layers were separated. The aqueous layer was extracted with methylene chloride (4×10 ml). The combined organic layers were washed with brine and dried ($MgSO_4$) and concentrated in vacuo. The obtained foamy solids were taken up in methylene chloride and placed upon a 24 cm×2.5 cm 40–63 µ silica column and eluted off with ethyl acetate (250 ml), 10% methanol/ethylacetate (250 ml), 20% methanol/ethylacetate (250 ml), and 10% methanol/methylene chloride (250 ml). The appropriate fractions were pooled to provide 1.082 g of 4-nitrobenzoic acid, 2-[4-[4-[5-[(acetylamino methyl]-2-oxo-3-oxazolidinyl]-2-fluorophenyl]-1-piperazinyl]-2-oxoethyl ester, (S)-; as a yellow solid in 82% yield (mp=222°–224° C.).

Next, 845 mg (1.555 mmol) of this product and 460 mg of 10% palladium on carbon was stirred in 100 ml of methanol/methylene chloride (1:1) under hydrogen (from a balloon) for 2 hours. The mixture was then filtered over diatomaceous earth and the filter pad washed with 70 ml of methanol/methylene chloride (1:1). The filtrate was concentrated in vacuo to provide 765 mg (96% crude yield) of foamy solids. A 550 mg portion of the solids was taken up in methylene chloride and placed upon a 9 cm×2.5 cm 70–230 mesh silica column. The column was eluted with 500 ml of 10% methanol/ethylacetate. Upon partial concentration of the combined fractions product was seen to precipitate. The precipitate was collected ty vacuum filtration to provide 352 mg of a white solid. A second crop (29 mg) of this compound was obtained upon concentration the filtrate. And concentration of the final filtrate provide 165 mg of the title compound as a glassy solid. In all 546 mg of the title compound was obtained from the column (99% recovery). The white solids became a glassy solid between 110° C. and 115° C. and a free flowing liquid at >215° C. Aqueous solubility (pH 7, phosphate buffer) was 0.03 mg/ml, although the salt version should be higher.

EXAMPLE 22

2,2-bis(hydroxymethyl)propionic acid, 2-[4-[4-[5-[(acetylamino)methyl]-2-oxo-3-oxazolidinyl]-2-fluorophenyl]-1-piperazinyl]-2-oxoethyl ester, (S)-

A solution of 183 mg (0.46 mmol) of the Intermediate of Ex. 1 and 146 mg (0.46 mmol) of 2,2-bis(benzyloxymethyl)propionic acid in 5 mL of pyridine was treated with 98 mg (0.51 mmol) of 1-ethyl-3-(3-dimethylaminopropyl)carbodiimide and 57 mg (0.46 mmol) of dimethylaminopyridine with stirring under nitrogen. After 72 h, the solvent was evaporated in vacuo to afford a yellow oil which was chromatographed over silica gel eluting with a methylene chloride-methanol system. These procedures afforded 82 mg (26%) of a white rigid foam. TLC: Rf=0.59 (20.1 methylene chloride-methanol).

A solution of this product 160 mg (0.23 mmol) of in 7 mL of methanol was treated under nitrogen with 50 mg of 10% palladium on carbon and hydrogen gas at atmospheric pressure. After 16 h, the mixture was filtered through celite and concentrated in vacuo to afford a colorless oil. This material was subjected to raidal chromatography eluting with a methylene chloride-methanol system to afford 99 mg (85%) of the desired product as a white rigid foam. TLC: Rf=0.26 (20:1methylene chloride-methanol. Aqueous solubility (pH 7, phosphate buffer) was 13 mg/ml.

EXAMPLE 23

Hydroxyacetic acid, 2-[4-[4-[5[(acetylamino)methyl]-2-oxo-3-oxazolidinyl]-2-fluorophenyl]-1-piperazinyl]-2-oxoethyl ester, (S)

To a mixture of 200 mg (0.508 mmol) of U-100592 (Ex. 1), 149 mg (1.47 mmol, 0.205 mL), and 5 mL methylene chloride at 0° C. benzyloxyacetylchloride was added dropwise. The reaction was allowed to warm slowly up to room temperature. After stirring for 5 hours, 5 mL of 1N HCl was added, and the resulting layers were separated. The aqueous layer was extracted with methylene chloride (3×5 mL). The combined organic layers were washed with brine and dried (MgSO$_4$) then filtered and concentrated to a white solid. The crude was dissolved in a small amount of methylene chloride and methanol and was placed on a 22 cm×2.5 cm 40–60 μ silica column. The column was eluted with ethyl acetate, 2% methanol/ethylacetate, 4% methanol/ethyl acetate, 6% methanol/ethyl acetate, 8% methanol/ethyl acetate, and 10% methanol/ethyl acetate (250 mL each). The appropriate fractions were pooled to provide 120 mg (44%) of benzyloxyacetic acid, 2-[-[4-[5-(acetylamino)methyl]-2-oxo-3-oxazolidinyl]-2-fluorophenyl]-1-piperazinyl]-2-oxoethyl ester, (S)-; as a white solid (mp=146°–148° C.).

A mixture of this product 170 mg (0.314 mmol), 15 mL methanol, 3 mL methylene chloride, and 100 mg 10% palladium catalyst. The reaction flask was evacuated with hydrogen 3 times and was allowed to stir under hydrogen overnight. The reaction was filtered by vacuum filtration with filter aid to remove the palladium catalyst and was concentrated to provide 130 mg (93% yield) of the title compound (mp=105°–107° C.). Aqueous solubility (pH 7, phosphate buffer) was 4.2 mg/ml.

EXAMPLE 24

Hydroxyacetic acid, 2-[4-[4-[5-[(acetylamino)methyl]-2-oxo-3-oxazolidinyl]-2,6-difluorophenyl]-1-piperazinyl]-2-oxoethyl ester, (S)-N-[[3-[3,5-difluoro-4-[4-(hydroxyacetyl)-1-piperazinyl]phenyl]-2-oxo-5-oxazolidinyl]methyl]acetamide (preparation described in Ex. 15) was used to prepare benzyloxyacetic acid, 2-[4-[4-[5[(acetylamino)methyl}-2-oxo-3-oxazolidinyl]-2,6-difluorophenyl]-1-piperazinyl]-2-oxoethyl ester, (S)-, in a 62% yield (mp=155°–157° C.) following the same procedure as for Example 23.

The subject compound was prepared from benzyloxyacetic acid, 2-[4-[4-[5-[(acetylamino)methyl]-2-oxo-3-oxazolidinyl]-2,6-difluorophenyl]-1-piperazinyl]-2oxoethyl ester, (S)-; in a 76% yield (mp=106°–108° C.) following the same procedure as for Ex. 23.

EXAMPLE 25

Methoxyacetic acid, 2-(4-(4-(5-((acetylamino)methyl)-2-oxo3-oxazolidinyl)-2-fluorophenyl)-1-piperazinyl)-2-oxoethyl ester, (S)

The (S)-N-[[3-[3-fluoro-4-[4-(hydroxyacetyl)-1-piperazinyl]phenyl]-2-oxo-5-oxazolidinyl]methyl] acetamide (263 mg, 0.67 mmol) was slurried in dry CH$_2$Cl$_2$ (10 mL) and cooled to 0° C. in an ice bath. The soluton became homogeneous after the addition of the pyridine (0.216 mL, 2.67 mmol). Next, the methoxyacetyl chloride (0.064 mL, 0.69 mmol) was added drop wise. The reaction was stirred at 0° C. for 30 minutes and then the ice bath was removed. After one hour, the reaction was found to be complete by TLC (10% MeOH/CHCl$_3$, UV short wave). The reaction mixture was diluted with CH$_2$Cl$_2$ (100 mL) and then washed with 1N HCl/brine (50 mL each), saturated NaHCO$_3$/brine (50 mL each), and brine (100 mL). Each aqueous portion was back-extracted with more CH$_2$Cl$_2$ (2×25 mL). The organic layers were combined, dried over anhydrous NaSO$_4$, filtered, and concentrated under reduced pressure to give an orange solid. This solid was chromatographed on silica gel (35 g,) eluting with a gradient of 1–5% MeOH in 10% CH$_3$CN/CHCl$_3$ to give an orange solid. The latter solid was recrystallized by dissolving it in a minimal amount of CH$_2$Cl$_2$/MeOH and then triturating with ether to yield 158 mg (51%) of the title compound as an off-white solid with a melting point of 147°–148° C. Aqueous solubility (pH 7, phosphate buffer) was 6.4 mg/ml.

EXAMPLE 26

3-(N-morpholinyl)propionic acid, 2-(4-(4-(5-((acetylamino)methyl)-2-oxo-3-oxaxzolidinyl)-2,6-difluorophenyl)-1-piperazinyl)-2-oxoethyl ester, (S)

(S)-N-[[3-[3,5-difluoro-4-[4-(hydroxyacetyl)-1-piperazinyl]phenyl]-2-oxo-5-oxazolidinyl]methyl] acetamide (preparation described in Ex. 15), 250 mg (0.607 mmol) was dissolved in 10 mL of pyridine. To this solution was added 13 mg of DMAP, 192 mg (1.21 mmol) 3-(N-morpholinyl)propionic acid and 232 mg (1.21 mmol) of 1-ethyl-3-(3-dimethylaminopropyl)carbodiimide hydrochloride. The reaction was allowed to stir at room temperature, under $N_2$ for 15 hours. After this time the reaction was complete and was concentrated in vacuo. The crude product was purified by silica gel chromatography (10 g of silica gel, eluted with 1–4% MeOH/$ChCl_3$). The recovered product (367 mg) contained a small amount of urea byproduct. A 250 mg portion of this material was further purified by radial chromatography (eluted with 1–66% MeOH/$CHCl_3$). After concentration, 210 mg of analytically pure product was recovered as a glassy, white solid. The title product (92%) was recovered as a glassy, white solid. mp: 139°–142° C.

FTIR(mull): $cm^{-1}$ 3450(br), 1754, 1665, 1514, 1450, 1247, 1120, 1032, 836.

Anal: Calc'd for $C_{25}H_{33}F_2N_5O_7$ ⅓ $H_2O$: C, 53.66; H, 6.02; N, 1252. Found: C, 53.66; H, 6.01; N, 12.55. Aqueous solubility (pH 7, phosphate buffer) was 8.2 mg/ml.

MS(EI):m/z(rel. int.) 553[$M^+$](1), 478(7), 229(19), 158 (17), 100(66), 56(53), 43(100). [α]=31 7° (c=9.67, $CHCl_3$).

EXAMPLE 27

(4-morpholinyl)acetic acid, 2-(4-(4-(5-((acetylamino)methyl)-2-oxo-3-oxazolidinyl)-2-fluorophenyl)-1-piperazinyl)-2-oxoethyl ester, (S)

A solution of 140 mg (0.272 mmol) of U-103676 in 3 mL of dry acetonitrile was treated with 52 mg (0.598 mmol) of morpholine with stirring for 18 hours. The off-white solid. This material was subjected to silica gel chromatrography eluting with a methanol-methylene chloride system to afford 115 mg (81%) of the desired product as a white solid. TLC: Rf=0.33 (20:1 Methylene chloride-methanol). Exact Mass: calc'd for $C_{24}H_{32}FN_5O_7$: 521.2286. Found: 521.2288. Aqueous solubility (pH 7, phosphate buffer) was 55.3 mg/ml.

EXAMPLE 28

4-N-(N,N-dimethylglycinyl)aminobenzoic acid, 2-[4-[4-[5-[(acetylamino)methyl]-2-oxo-3-oxazolidinyl]-2-fluorophenyl]-1-piperazinyl]-2-oxoethyl ester, (S)-

A mixture of 204 mg (01.398 mmol) of the title compound from Ex. 21, catalytic amount (<10 mg) of 4-dimethylamino pyridine (DMAP), 156 mg (0.814 mmol) of 1-ethyl-3-(3-dimethylaminopropyl) carbodiimide and 147 mg (1.05 mmol) of temperature. The mixture was then concentrated in vacuo. The obtained crude was treated with 5 ml saturated aqueous sodium bicarbonate and 20 ml of water and extracted with methylene chloride (4×20 ml). The combined organic layers were washed with brine, dried ($MgSO_4$) and purified on a 23 cm×2.5 cm, 40–63 μ silica gel column eluting with 5% methanol/methylene chloride (1 L) to provide 175 mg (74%) of the desired product as foamy solids. Trituation with 10% methanol/ethylacetate of foamy solids from a different lot provided white solids with mp=180°–182° C. Aqueous solubility (pH 7, phosphate buffer) was 0.09 mg/ml, although the salt version should be higher.

EXAMPLE 29

4-N-(glycinyl)aminobenzoic acid, 2-[4-[4-[5-[(acetylamino)methyl]-2-oxo-3-oxazolidinyl]-2-fluorophenyl]-1-piperazinyl]-2-oxoethyl ester, (S)-

Step 1

A mixture of 100 mg (0.195 mmol) of the title compound from Ex. 21, 243 mg (1.27 mmol) of 1-ethyl-3-(3-dimethylaminopropyl) carbodiimide and 269 mg (1.29 mmol) of N-CBZ-glycine in 4.0 ml of pyridine with a catalytic amount (<10 mg) of 4-dimethylamino pyridine (DMAP), was stirred over night at room temperature. The mixture was then concentrated in vacuo and the obtained crude was purified on a 23 cm×2.5 cm, 40–63 μ silica gel column eluting with a methanol:methylene chloride gradient (500 ml 2.5% MeOH/$CH_2Cl_2$, 500 ml 5% MeOH/$CH_2Cl_2$, 500 ml 10% MeOH/$CH_2Cl_2$) to provide 135 mg (99%) of 4-N-(N-carbobenzyl-oxyglycinyl) aminobenzoic acid, 2-[4-[4-[5-[(acetylamino)methyl]-2-oxo-3-oxazolidinyl]-2-fluorophenyl]-1-piperazinyl]-2-oxoethyl ester, (s)- as white solids. Analysis Calc.: C, 59.65; H, 5.29; N, 11.93. Found: C, 59.37; H, 5.35; N, 11.54.

Step 2

A mixture of this product 275 mg (0.391 mmol) and 170 mg of 10% palladium on carbon in 75 ml methanol and 55 ml of methylene chloride was stirred over night under hydrogen (balloon). The mixture was then filtered over diatomaceous earth and the filtrate concentrated in vacuo. The obtained solids were triturated with methanol in a warm water bath then the mixture was cooled and the solids were collected by vacuum filtration to provide 211 mg (95% yield) of the desired product as off white solids (mp 240° C. decomposition). Aqueous solubility (pH 7, phosphate buffer) was 9.8 mg/ml.

EXAMPLE 30

Acetic acid, 2-[4-[4-[5-[(acetylamino)methyl]-2-oxo-3-oxazolidinyl]-2-fluorophenyl]-1-piperazinyl]-2-oxoethyl ester, (S)-

A mixture of 519 mg of the Intermediate from Ex. 1 in 2.5 ml acetic anhydride and 10 ml pyridine was stirred at room temperature for 2 hr. The mixture was concentrated in vacuo to a white solid, and this was purified on a 24.5 cm×2.5 cm, 40–63 μ silica gel column, eluting with 500 ml of 10% methanol/ethylacetate and 400 ml 15% methanol/ethylacetate (25 ml fractions). The appropriate fractions were pooled and concentrated in vacuo to provide 540 mg (94%) of the title compound as a foamy white solid. The solid was triturated with 15 ml of 10% methanol/ethylacetate and the solids were collected by vacuum filtration and dried in a vacuum oven to provide 436 mg (76%) of the title compound as a fine white powder (mp= 199°–201° C.)

What is claimed:

1. A compound of structural Formula I:

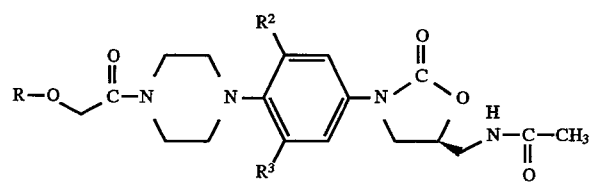

or pharmaceutically acceptable salts thereof wherein:

R is —C(O)—$R^1$, —$PO_3^=$ or —P(O)(OH)$_2$:

$R^1$ is $C_{1-6}$alkyl, —N($R^4$)$_2$, $C_{1-6}$alkyl-N($R^4$)$_2$, -phenyl-N($R^4$)$_2$, -phenyl-NCH(O)$CH_2NH_2$, —$C_2H_4$-morpholinyl, pyridinyl, $C_{1-6}$alkyl-OH, $C_{1-6}$alkyl-OCH$_3$, $C_{1-6}$alkyl C(O)CH$_3$, —O—$C_{1-6}$alkyl-OCH$_3$, $C_{0-3}$alkyl-piperazinyl (optionally substituted with $C_{1-3}$alkyl), imidazolyl, $C_{1-6}$alkyl-COOH, —C(CH$_2$OH)$_2$CH$_3$;

R² and R³ are independently selected from hydrogen or F except at least one of R² or R³ is F;

R⁴ are independently selected from hydrogen or $C_{1-6}$alkyl.

2. The compound of claim 1 wherein R is —C(O)—R¹.

3. The compound of claim 2 wherein R¹ is —CH₃, —CH₂N(CH₃)₂, —C₂H₄— morpholinyl or —CH₂OH.

4. The compound of claim 1 wherein R is —P(O)(OH)₂.

5. The compound of claim 1 wherein R is —PO₃⁼.

6. The compound of claim 1 which is an optically pure enantiomer having the S- configuration at C5 of the oxazolidione ring.

7. The compound of claim 1 wherein one of R² and R³ is F and the other is hydrogen.

8. The compound of claim 1 which is:

1) 3-(4-Morpholinyl)propionic acid, 2-(4-(4-(5-((acetylamino)methyl)-2-oxo-3-oxazolidinyl)-2-flurophenyl)-1-piperazinyl)-2-oxoethyl ester, (S);

2) Nicotinic acid, 2-[4-[4-5-[(acetylamino)methyl]-2oxo-3-oxazolidinyl]-2-fluorophenyl]-1-piperazinyl]-2-oxoethyl ester, (S)-;

3) Nicotinic acid 2-[4-[4-[5-[(acetylamino)methyl]-2oxo-3-oxazolidinyl]-2,6-difluorophenyl]-1-piperazinyl]-2-oxoethyl ester, (S)-;

4) 1H-imidazole-1-carboxylic acid, 2-[4-[4-[5-[(acetylamino)methyl]-2oxo-3-oxazolidinyl]-2-fluorophenyl]-1-piperazinyl]-2-oxoethyl ester, (S)-;

5) 1H-imidazole-1-carboxylic acid, 2-[4-[4-[5-[(acetylamino)methyl]-2oxo-3-oxazolidinyl]-2,6-difluorophenyl]-1-piperazinyl]-2-oxoethyl ester, (S)-;

6) Carbonic acid, 2-[4-[4-[5-[(acetylamino)methyl]-2oxo-3-oxazolidinyl]-2-fluorophenyl]-1-piperazinyl]-2-oxoethyl ester-2-methoxyethyl ester, (S);

7) 4-dimethylaminobenzoic acid, 2-[4-[4-[5-[(acetylamino)methyl]-2oxo-3-oxazolidinyl]-2-fluorophenyl]-1-piperazinyl]-2-oxoethyl ester, (S)-;

8) 4-dimethylaminobenzoic acid, 2-[4-[4-[5-[(acetylamino)methyl]-2oxo-3-oxazolidinyl]-2,6-difluorophenyl]-1-piperazinyl]-2-oxoethyl ester, (S)-;

9) Glycine, N,N-dimethyl-, 2-[4-[4-[5-[(acetylamino)methyl]-2oxo-oxazolidinyl]-2-fluorophenyl]-1-piperazinyl]-2-oxoethyl ester, (S)-;

10) Glycine, N,N-dimethyl-, 2-[4-[4-[5-[(acetylamino)methyl]-2oxo-3-oxazolidinyl]-2,6-difluorophenyl]-1-piperazinyl]-2-oxoethyl ester, (S)-;

11) 3-(Dimethylamino)propanoic acid, 2-[4-[4-[5-[(acetylamino)methyl]-2oxo-3-oxazolidinyl]-2-fluorophenyl]-1-piperazinyl]-2-oxoethyl ester, (S)-;

12) 4-(Dimethylamino)butanoic acid, 2-[4-[4-[5-[(acetylamino)methyl]-2oxo-3-oxazolidinyl]-2-fluorophenyl]-1-piperazinyl]-2-oxoethyl ester, (S)-;

13) (4-Methyl-1-piperazinyl)acetic acid, 2-[4-[4-[5-[(acetylamino)methyl]-2oxo-3-oxazolidinyl]-2-fluorophenyl]-1-piperazinyl]-2-oxoethyl ester, (S)-;

14) Acetic acid, 2-(4-(4-(5-((acetylamino)methyl)-2-oxo-3-oxazolindinyl)-2,6-difluorophenyl)-1-piperazinyl)-2-oxoethyl ester, (S);

15) Succinic acid, 2-(4-(4-(5-((acetylamino)methyl)-2-oxo-3-oxazolidinyl)-2,6-difluorophenyl)-1-piperazinyl)-2-oxoethyl monoester, (S);

16) Succinic acid, 2-(4-(4-(5-((acetylamino)methyl)-2-oxo-3-oxazolidinyl)-2,6-difluorophenyl)-1-piperazinyl)-2-oxoethyl monoester, sodium salt (S);

17) Succinic acid, 2-(4-(4-(5-((acetylamino)methyl)-2-oxo-3-oxazolidinyl)-2,6-difluorophenyl)-1-piperazinyl)-2-oxoethyl monoester, (S);

(18) 4-Oxo-valeric acid, 2-(4-(4-(5-((acetylamino)methyl)-2-oxo-3-oxazolidinyl)-2,6-difluorophenyl)-1-piperazinyl)-2-oxoethyl ester, (S);

19) 4-Oxo-valeric acid, 2-(4-(4-(5-((acetylamino)methyl)-2-oxo-3-oxazolidinyl)-2-fluorophenyl)-1-piperazinyl)-2-oxoethyl monoester, (S);

20) Phosphoric acid, 2-(4-(4-(5-((acetylamino)methyl)-2-oxo-3-oxazolidinyl)-2-fluorophenyl)-1-piperazinyl)-2-oxoethyl ester, (S);

21) 4-aminobenzoic acid, 2-[4-[4-[5-[(acetylamino)methyl]-2oxo-3-oxazolidinyl]-2-fluorophenyl]-1-piperazinyl]-2-oxoethyl ester, (S)-;

22) 2,2-bis(hydroxymethyl)propionic acid, 2-[4-[4-[5-[(acetylamino)methyl]-2oxo-3-oxazolidinyl]-2-fluorophenyl]-1-piperazinyl]-2-oxoethyl ester, (S)-;

23) Hydroxyacetic acid, 2-[4-[4-[5-[(acetylamino)methyl]-2oxo-3-oxazolidinyl]-2-fluorophenyl]-1-piperazinyl]-2-oxoethyl ester, (S);

24) Hydroxyacetic acid, 2-[4-[4-[5-[(acetylamino)methyl]-2oxo-3-oxazolidinyl]-2,6-difluorophenyl]-1-piperazinyl]-2-oxoethyl ester, (S)-;

25) Methoxyacetic acid, 2-(4-(4-(5-((acetylamino)methyl)-2-oxo-3-oxazolidinyl)-2-fluorophenyl)-1-piperazinyl)-2-oxoethyl ester, (S);

26) 3-(N-morpholinyl)propionic acid, 2-(4-(4-(5-((acetylamino)methyl)-2-oxo-3-oxazolidinyl)-2,6-difluorophenyl)-1-piperazinyl)-2-oxoethyl ester, (S);

27) 4-N-(glycinyl)aminobenzoic acid, 2-[4-[4-[5-[(acetylamino)methyl]-2oxo-3-oxazolidinyl]-2-fluorophenyl]-1-piperazinyl]-2-oxoethyl ester, (S)-; or 28) Acetic acid, 2-[4-[4-[5-[(acetylamino)methyl]-2oxo-3-oxazolidinyl]-2-fluorophenyl]-1-piperazinyl]-2-oxoethyl ester, (S)-.

9. A method for treating microbial infections in warm blooded animals comprising:

administering to a patient in need thereof a pharmaceutically effective amount of a compound of Formula I.

10. The method of claim 9 wherein said compound is administered in an effective amount of from about 0.1 to about 100 mg/kg of body weight/day.

11. The method of claim 10 wherein said compound is administered in an amount of from about 3.0 to about 50 mg/kg of body weight/day.

12. A compound selected from the group consisting of:

(4-morpholinyl)acetic acid, 2-(4-(4-(5-((acetylamino) methyl-2-oxo-3oxazolidinyl-2-fluorophenyl)-1-piperazinyl)-2-oxoethyl ester, (S); and 4-N-(N,N-dimethylglycinyl)aminobenzoic acid, 2-[4-[4-[5-[(acetylamino)methyl]-2oxo-3-oxazolidinyl]-2-fluorophenyl]-1-piperazinyl]-2-oxoethyl ester, (S).

* * * * *